United States Patent [19]

Hayden et al.

[11]  4,226,782
[45]  Oct. 7, 1980

[54] PRODUCTION OF ALKYLENE OXIDES AND CATALYSTS THEREOF

[75] Inventors: Percy Hayden; Richard W. Clayton, both of Middlesbrough, England; Alan F. G. Cope, Cheltenham, Australia

[73] Assignee: Imperial Chemical Industries Limited, London, England

[21] Appl. No.: 903,403

[22] Filed: May 8, 1978

[30] Foreign Application Priority Data

May 23, 1977 [GB] United Kingdom ............... 21611/77

[51] Int. Cl.³ ..................... C07D 301/10; B01J 23/04; B01J 23/50
[52] U.S. Cl. .............................. 260/348.34; 252/463; 252/476
[58] Field of Search ............................... 252/463, 476; 260/348.34

[56]  References Cited

U.S. PATENT DOCUMENTS

| 3,962,136 | 6/1976 | Nielsen et al. ................... 252/463 X |
| 4,007,135 | 2/1977 | Hayden et al. ................... 252/476 X |
| 4,010,115 | 3/1977 | Nielsen et al. ................... 252/476 X |
| 4,033,903 | 7/1977 | Maxwell ............................. 252/476 |
| 4,066,575 | 1/1978 | Winnick ............................ 252/476 X |

Primary Examiner—W. J. Shine
Attorney, Agent, or Firm—Cushman, Darby & Cushman

[57]  ABSTRACT

Catalysts for the oxidation of alkenes to alkylene oxides comprise silver on supports having a surface area of 0.05 to 10 m²/g, and at least 16 μg equivalents per square meter of potassium together with rubidium and/or cesium.

8 Claims, No Drawings

PRODUCTION OF ALKYLENE OXIDES AND CATALYSTS THEREOF

This invention relates to the production of alkylene oxides and catalysts therefor.

The invention provides catalysts for the production of alkylene oxides for example ethylene and propylene oxides by oxidation of the corresponding olefine with oxygen which comprise silver supported on a porous heat resisting support which has a specific surface area in the range 0.05 to 10 m$^2$/g and preferably 0.1 to 5 m$^2$/g and more preferably 0.3 to 5 m$^2$/g as measured by the Brunauer Emmett and Teller Method, the catalyst also comprising more than 16 μgram equivalents of potassium per square meter of surface area of the catalyst the said amount being also more than $1.5 \times 10^{-5}$ gram equivalents per gram of catalyst together with at least one other alkali metal selected from rubidium and cesium, the said potassium, rubidium and cesium being present in a form which is extractable by contact with water. The potassium and rubidium and/or cesium act as promotors, i.e. components of the catalyst which increase the activity or preferably selectivity of the catalyst at any time in the life of the catalyst; the initial selectivity may for example thus be higher and/or it may be maintained for longer.

The support is suitably a preformed support.

Silver may be introduced to a pre-formed porous heat resisting support as a suspension of silver or silver oxide in a liquid medium for example water or by impregnation of the support with a solution of a silver compound which can be reduced to silver metal if necessary by means of a reducing agent for example hydrogen. If necessary a heat treatment may be used to decompose the silver compound to silver. Suitably the impregnating solution contains a reducing agent which may be for example an anion, for example a formate, acetate, propionate, lactate, tartarate or preferably oxalate ion, of a silver compound in the solution. The reducing agent may be for example an aldehyde, for example formaldehyde or acetaldehyde or an alcohol preferably having 1 to 4 carbon atoms for example methanol or ethanol.

The solution may be a solution in water and/or an organic solvent, for example an aliphatic alcohol preferably having 1 to 4 carbon atoms, a polyhydric alcohol for example ethylene glycol or glycerol, a ketone for example acetone, an ether for example dioxan or tetrahydrofuran, a carboxylic acid for example acetic acid, or molten lactic acid which is preferably used in the presence of water, or an ester for example ethyl acetate or a nitrogen containing base for example pyridine or formamide. An organic solvent may function as a reducing agent and/or complexing agent for the silver also.

If the silver is introduced by impregnating a support with a solution of a decomposable silver compound it is preferred that ammonia and/or a nitrogen containing base should be present. The nitrogen containing base suitably acts as a ligand maintaining the silver in solution; for example it may be pyridine, acetonitrile, an amine, especially a primary or secondary amine having 1-6 carbon atoms, or preferably ammonia. Other suitable nitrogen-containing bases include acrylonitrile, hydroxylamine and alkanolamines for example ethanolamine, alkylene diamines having from 2-4 carbon atoms or amides for example formamaide or dimethyl formamide. The nitrogen-containing bases may be used alone or in admixture, mixtures of ammonia and a second nitrogen containing base being preferred. Suitably the nitrogen containing base or bases are used together with water.

Alternatively the solution may be a neutral or acid solution for example it may be a solution of a silver carboxylate especially a formate, acetate, propionate, oxalate, citrate, tartarate or preferably lactate or for example a solution of silver nitrate.

The solutions preferably contain 3-50% of silver by weight.

Impregnation may be carried out in a single stage or if desired may be repeated one or more times. By this means higher silver contents of the catalyst may be achieved.

The silver compound may generally be reduced to silver by heating in the range 100° to 350° C., for example for a period of 15 mins to 4 hours, preferably in the substantial absence of oxygen, for example in the presence of an inert gas for example nitrogen.

The catalyst support preferably has an apparent porosity as measured by the mercury absorption method of at least 20%, for example 30–80% preferably 30–65% and more preferably 40–60% and mean pore diameters of 0.1 to 20 microns preferably 0.3 to 4 microns as measured by the mercury porosimetry method. The pore size distribution of the support may be bimodal, in which case the smaller pores preferably account for at least 70% of the total pore volume and have a mean pore diameter preferably in the range of 0.1 and preferably 0.3 to 4 microns, and the larger pores preferably have a mean pore diameter in the range 25 to 500 microns.

Most of the silver content of the catalyst is preferably present in the form of discrete particles adhering to the support having equivalent diameters of less than 10,000 Å preferably in the range 20–10,000 Å and more preferably 40–8,000 Å. By equivalent diameter is meant the diameter of a sphere of the same silver content as the particle.

Preferably at least 80% of the silver is present as particles having equivalent diameters in the aforesaid range, the quantity of silver being judged in terms of the number of particles falling in that range. The silver may be present as silver and/or silver oxide and is thought to be present normally as silver particles having a surface layer of silver oxide. The dimensions of the silver particles may be determined by scanning electron microscopy.

The support may be an alumina, silicon carbide, silica, zirconia or silica/alumina support, but it is preferably composed of an aggregate of alpha-alumina particles which may be fused together or cemented together with, for example, silica or baryta.

The catalyst preferably comprises 3 to 50% and more preferably 15 to 30% by weight of silver.

The preferred levels of potassium and rubidium and/or cesium in a form which is extractable by contact with water are related to the surface area of the support. The preferred level of potassium expressed as microgram equivalents per gram of catalyst is K'S where K' is a constant preferably in the range 16 to 2000, more preferably 30 to 500, and S is the surface area of the support in square meters per gram. The preferred level for rubidium expressed as a microgram equivalents per gram of the catalyst is K"S where K" is a constant in the range 0.5 to 40, more preferably 1 to 20 for example in the range 2 to 12 and S is as before defined. The preferred level of cesium expressed as microgram equivalents per gram of catalyst is $K'''S$ where $K'''$ is a constant in the range 0.3 to 25, more preferably 0.5 to 10 for example 1 to 6 and S is as before defined. The preferred atomic ratio of potassium to rubidium and cesium taken together is 1.5:1 to 200:1.

The form in which the potassium, rubidium and cesium is present is determined by the conditions under which an oxidation of an olefine to an olefine oxide is carried out using the catalyst. The alkali metal may be introduced as any suitable compound for example a carbonate, hydroxide, bicarbonate, lower carboxylate for example acetate or oxalate or preferably a nitrate. It is preferred that catalyst poisons, for example bromine, iodine and sulphur are substantially absent.

The promoters may be introduced to the support before during or after impregnation with a solution of the silver compound. The promoters are suitably introduced as solutions of compounds of the promoting elements, which solutions may be in water and/or organic solvents. They may comprise solvents, reducing agents and/or complexing agents as previously described. If it is desired to impregnate a catalyst which has already been used in the oxidation of an alkene to an alkylene oxide and has lost performance, this may be carried out also, whether or not the catalyst already contains one or more promoters. It may also be possible to regenerate a catalyst according to the invention which has deteriorated in performance in use by contacting it with water and/or an organic solvent as previously described. The catalyst after treatment as aforesaid is heated to a temperature at which promotion becomes effective, normally in the range 100° to 350° C.; such heating may serve to decompose the silver compound if present also.

The invention also provides processes for the production of alkylene oxides for example ethylene and propylene oxides by the oxidation of the corresponding olefine with oxygen using a catalyst as aforesaid.

Partial pressures of ethylene or propylene in such processes may be in the ranges 0.1-30 and preferably 1 to 30 bars. The total pressure may be in the range of from 1 to 100 and preferably 3-100 bars absolute. The molar ratio of oxygen to ethylene or propylene may be in the range 0.05 to 100. The partial pressure of oxygen may be in the range 0.01 and preferably 0.1 to 20 bars and preferably 1-10 bars. The oxygen may be supplied for example in the form of air or preferably as commercial oxygen. A diluent for example helium, nitrogen, argon and/or carbon dioxide and/or preferably methane may be present in proportions of 10-80% and preferably 40-70% by volume in total. It is necessary to operate using gas compositions which are outside the explosive limits.

The temperature is suitably in the range 200°–300° C., and preferably in the range 220°–290° C. Contact times should be sufficient to convert 0.5-70%, for example 2 to 20 and preferably 5-20% of the ethylene or propylene and unconverted ethylene or propylene is suitably recycled.

A reaction modifier is suitably present. Suitable reaction modifiers comprise chlorine and may be for example chlorinated alkenes having 1-6 carbon atoms for example methyl chloride or tertiary butyl chloride, di-chloromethane or chloroform, a chlorinated biphenyl or polyphenyl, a chlorinated benzene which may be for example monochloro- or dichloro-benzene, or especially ethylene dichloride. The concentration of the reaction modifier depends on its chemical nature for example in the case of ethylene dichloride 0.1 to 100 and preferably 0.5-25 parts per million by weight are normally present and in the case of vinyl chloride 0.1 to 200 and preferably 5 to 80 parts per million by weight are suitably present.

We have found that with appropriate concentrations of such reaction modifiers, especially vinyl chloride, attractive selectivities may be secured.

EXAMPLE 1

Catalysts A-I for the oxidation of ethylene and propylene to ethylene oxide and propylene oxide were prepared as follows:

5.2 g of reagent grade silver acetate were dissolved in the minimum amount of ammonia required to give complete dissolution. Appropriate amounts of potassium acetate, rubidium carbonate and/or cesium carbonate were added to this solution and the volume of the solution was made up to 6 ml by the addition of water. This solution was used to impregnate 30 g. of the support material. The support used was an alpha-alumina composite sold by Norton Co. under the trade-mark ALUNDUM which had previously been crushed and sieved to give particles with diameters in the range 0.42-1 mm. The surface area of this material was 0.3 $m^2g^{-1}$, the mean pore diameter was 2.8 microns and the water porosity was 20%.

The support impregnated with the silver solution was heated in a forced draught oven for 4 hours. During this time the temperature of the oven was raised from 100° to 300° C. This procedure results in catalysts containing about 8% silver by weight. The levels of potassium, rubidium and cesium for the various catalysts are given in Table 1.

EXAMPLE 2

The catalysts prepared by the method described in Example 1 were tested for catalytic activity in the following manner:

20 g. of catalyst was loaded into a stainless steel reactor (internal diameter 8 mm) contained in a thermostatically controlled fluidised bed. The catalyst was conditioned for a period of 24 hours under increasingly severe reaction conditions. Once it had reached a steady performance the selectivity to ethylene oxide and oxygen conversion were measured using a process gas stream containing 30% ethylene, 8% oxygen and 30 ppm vinyl chloride at a pressure of 15 p.s.i.a. The temperature of the reactor was 240° C. and the gas hourly space velocity 400 $hr^{-1}$.

The process gas pressure was then raised to 240 p.s.i.a. and the selectivity and oxygen conversion measured at 240° C. and a GHSV of 4000 $hr^{-1}$ once the catalyst performance had stabilised again.

The results of the catalyst tests are shown in Table 1.

EXAMPLE 3

Catalysts J-N for the oxidation of ethylene and propylene to ethylene oxide and propylene oxide were prepared as follows:

8.9 gm of silver oxalate were dissolved in 7 mls of a solution of 50%, 1,2 diaminoethane in water. The resulting solution was made up to 8 mls by the addition of ethanolamine. Appropriate amounts of potassium acetate, rubidium carbonate and/or cesium carbonate were added to this solution which was then used to impregnate 20 g. of the support material. The support used was a porous alpha-alumina in the form of cylindrical pellets 3 mm diameter and 3 mm long. The surface area was 2.2 $m^2g^{-1}$, the mean pore diameter was 1 micron and the pore volume was 0.5 ml $g^{-1}$.

The impregnated support was heated at 290° C. for a period of 3 hours in a forced draught air oven. This procedure resulted in catalysts containing about 24% by weight of silver. The levels of potassium, rubidium and cesium present in the final catalyst are given in Table 1.

EXAMPLE 4

The catalysts prepared in Example 3 were tested for activity in the following way:

10 g. of catalyst were loaded into a stainless steel reactor (internal diameter 8 mm). The catalyst was subjected to increasingly severe reaction conditions and, once the performance had stabilised, the catalyst selectivity and oxygen conversion were measured using a process gas stream containing 30% ethylene, 8% oxygen and 30 ppm vinyl chloride. The temperature of the reactor was 240° C. and the gas hourly space velocity (GHSV) was 2,000 $hr^{-1}$.

The process gas pressure was then raised to 240 p.s.i.a. and the selectivity and oxygen conversion measured at 240° C. at a gas hourly space velocity of 15,000 $hr^{-1}$ after the catalyst performance had stabilised again. The results of the catalyst tests are shown in Table 1.

EXAMPLE 5

Catalysts 1A-1L were prepared by the following method.

5.2 g reagent grade silver acetate were dissolved in the minimum amount of ammonia required to give complete dissolution. Appropriate amounts of potassium nitrate and rubidium nitrate were added to this solution and the volume was made up to 6 ml by the addition of water. This solution was used to impregnate 30 g of the support material. The support used was an alpha-alumina composite sold by Norton Co. under the trade mark ALUNDUM which had previously been crushed and sieved to give particles with diameters in the range 0.42–1.0 mm. The surface area of this material was 0.3 $m^2g^{-1}$, the mean pore diameter was 2.8 microns and the water porosity was 20%.

The support impregnated with the silver solution was heated in a forced draught oven for 3 hours at a temperature of 290° C. This procedure results in catalysts containing about 8% silver by weight. The potassium and rubidium contents are given in Table 2.

EXAMPLE 6

Catalysts prepared in Example 5 were tested for activity in the following way:

20 g of catalyst were loaded into a stainless steel reactor (internal diameter 8 mm). The catalyst was subjected to increasingly severe reaction conditions and, once the performance had stabilised, the catalyst selectivity and oxygen conversion were measured using a process gas stream containing 30% ethylene, 8% oxygen, 20 ppm vinyl chloride and 62% nitrogen at a pressure of 240 p.s.i.a. The temperature of the reactor was 240° C. and the GHSV was 3,000 $hr^{-1}$. The results of the catalyst tests are given in Table 2.

TABLE 1

| Catalyst | Promoter levels (wt %) K | Rb | Cs | Selectivity @ 15 psia (%) | Oxygen Conversion @ 15 psia (%) | Selectivity @ 240 psia (%) | Oxygen Conversion @ 240 psia (%) |
|---|---|---|---|---|---|---|---|
| A | 0.1 | 0.001 | — | 92 | 9 | 91 | 9 |
| B | 0.1 | 0.003 | — | 92 | 11 | 89 | 6 |
| C | 0.1 | 0.01 | — | 92 | 9 | 90 | 6 |
| D | 0.1 | 0.03 | — | 90 | 8 | 90 | 8 |
| E | 0.1 | 0.03 | — | 91 | 8 | 90 | 9 |
| F | 0.1 | 0.01 | — | 91 | 5 | 90 | 6 |
| G | 0.1 | — | 0.003 | 93 | 8 | 88 | 7 |
| H | 0.1 | — | 0.010 | 93 | 5 | 90 | 6 |
| J | 0.3 | .015 | — | 93 | 20 | 90 | 4 |
| K | 0.3 | .06 | — | 92 | 15 | 89 | 2 |
| L | 0.3 | .15 | — | 92 | 5 | 88 | 2 |
| COMPARATIVE EXAMPLES | | | | | | | |
| I | 0.03 | — | — | 80 | 10 | 80 | 10 |
| M | 0.02 | — | — | 85 | 10 | 80 | 10 |
| N | 0.10 | — | — | 87 | 10 | 81 | 6 |

GHSV = Gas hourly space velocity
psia = pounds per square inch absolute

TABLE 2

| Catalyst | Promoter levels (wt %) K | Rb | Selectivity (%) | Oxygen Conversion (%) |
|---|---|---|---|---|
| 1A | 0.3 | 0.001 | 94 | 9 |
| 1B | 0.3 | 0.003 | 92 | 5 |
| 1C | 0.3 | 0.01 | 93 | 6 |
| 1D | 0.3 | 0.03 | 91 | 5 |
| 1E | 0.1 | 0.001 | 93 | 8 |
| 1F | 0.1 | 0.003 | 92 | 7 |
| 1G | 0.1 | 0.01 | 93 | 8 |
| 1H | 0.1 | 0.03 | 91 | 7 |
| COMPARATIVE EXAMPLES | | | | |
| 1I | 0.03 | 0.01 | 84 | 4 |
| 1J | 0.03 | 0.03 | 82 | 3 |
| 1K | 0.01 | 0.001 | 84 | 10 |
| 1L | 0.01 | 0.003 | 85 | 9 |

Gas compositions are expressed as % by volume
GHSV = Gas hourly space velocity
psia = pounds per square inch absolute
Selectivities are yields of ethylene oxide based on ethylene converted.
ppm = parts per million by weight

We claim:

1. A catalyst for the production of an alkylene oxide by oxidation of the corresponding olefine with oxygen which comprises silver supported on a porous heat resisting support which has a specific surface area in the range 0.05 to 10 $m^2/g$ as measured by the Brunauer Emmett and Teller method, the catalyst also comprising more than 16 μgram equivalents of potassium per square meter of surface area of the catalyst, the said amount being also more than $1.5 \times 10^{-5}$ gram equivalents per gram of catalyst, together with at least one other alkali metal selected from rubidium and cesium, the said potassium and rubidium and/or cesium being present in a form which is extractable by contact with water.

2. A catalyst as claimed in claim 1 in which the porous heat resisting support has a specific surface area in the range 0.3 to 5 $m^2/g$.

3. A catalyst as claimed in claim 1 of which the support has an apparent porosity as measured by the mercury absorption method of 30–80%, and pores of 0.1 to 20 microns as measured by the mercury porosimetry method.

4. A catalyst as claimed in claim 1 in which the support is composed of an aggregate of alpha-alumina particles which are fused or cemented together and which comprises 3 to 50% by weight of silver.

5. A catalyst as claimed in claim 1 in which the atomic ratio of potassium to rubidium and cesium taken together in a form which is extractable by contact with water is 1.5:1 to 200:1.

6. A process of producing a catalyst as claimed in claim 1 which comprises impregnating a suitable support with a solution of a silver compound, introducing compounds of said potassium and said other alkali metal before, during or after the impregnation with the solution of the silver compound, and reducing the silver compound.

7. A process as claimed in claim 6 in which the solution comprises water and a nitrogen-containing base.

8. A process for the production of an alkylene oxide by oxidation of the corresponding olefine with oxygen in the presence of a catalyst as claimed in claim 1.

* * * * *